United States Patent [19]
Hampton, Sr.

[11] Patent Number: 5,147,575
[45] Date of Patent: Sep. 15, 1992

[54] COMPOSITION AND METHOD FOR CLEANING AND LUBRICATING HAIR SHEARS

[76] Inventor: Ronald S. Hampton, Sr., 7095 Winkfield Pl., College Park, Ga. 30349

[21] Appl. No.: 745,001

[22] Filed: Aug. 14, 1991

Related U.S. Application Data

[63] Continuation-in-part of Ser. No. 402,628, Sep. 9, 1989, abandoned, which is a continuation-in-part of Ser. No. 181,054, Apr. 13, 1988, abandoned.

[51] Int. Cl.$^5$ .................. C11D 7/50; C11D 3/48; C11G 5/032
[52] U.S. Cl. .................. 252/171; 252/162; 252/172; 252/170; 252/174.15; 252/106
[58] Field of Search ............... 252/162, 172, 170, 171, 252/174.11, 174.15, 106

[56] References Cited

U.S. PATENT DOCUMENTS

| | | | |
|---|---|---|---|
| 3,634,236 | 1/1972 | Buster et al. | 252/8.9 |
| 4,336,270 | 6/1982 | Muntwyler | 252/106 |
| 4,708,807 | 11/1987 | Kemerer | 252/174.15 |
| 4,808,329 | 2/1989 | Soldanski et al. | 252/171 |
| 4,859,359 | 8/1989 | DeMatteo et al. | 252/171 |

*Primary Examiner*—A. Lionel Clingman
*Assistant Examiner*—Bradley A. Swope

[57] ABSTRACT

A solution for cleaning and lubricating hair shears and the like contains a nonchlorinated aliphatic hydrocarbon, dimethylpolysiloxane, mineral oil, a small amount of fragrance and a small amount of an antimicrobial agent. The blades (14) of hair shears (12) are immersed in the solution (10) and oscillated to loosen and remove fouling particles. The shears are then withdrawn from the solution and excess solution is removed to ready the clippers for use.

6 Claims, 1 Drawing Sheet

COMPOSITION AND METHOD FOR CLEANING AND LUBRICATING HAIR SHEARS

CONTINUATION APPLICATION

This application is a continuation-in-part of application No. 07/402,628, Filed Sep. 9, 1989, which was a continuation-in-part of application No. 07/181,054, Filed Apr. 13, 1988, both now abandoned.

This invention relates generally to compositions and methods for cleaning, and more particularly, relates to a composition and method for cleaning and lubricating hair shears and the like.

BACKGROUND OF THE INVENTION

Shears that are used for grooming hair have blades that are used to clip or cut the hair. Cutting is effected by movement or oscillation of the blades relative to one another. Through use, the blades of the shears become fouled by hair particles, dirt, body oils, hair grooming preparations and other miscellaneous, undesirable particles that may become lodged in the hair.

Fouling of the blades hinders the efficient operation and use of the shears. Material which fouls blades can be abrasive enough to dull the blades as they move or oscillate. Dull blades do not cut hair efficiently. They tend to pull hair rather than cut, causing pain and discomfort to the person whose hair is being cut. The pulling action can then cause the shears' blades to pinch or abrade the scalp. This causes additional pain and discomfort and also creates the possibility for germs to infect the scalp through the pinched or abraded area. As can be seen, fouling requires that blades be sharpened more frequently.

The operation of shears is further hindered by fouling in that there is greater friction between fouled blades than clean blades. There is a certain amount of friction and temperature increase which is caused by general movement of the blades relative to one another; however, the greater friction causes the temperature of blades to increase even more, possibly beyond design parameters. The hotter blades are more easily dulled by abrasive foreign particles. In addition, if there is sufficient friction caused, the blades can become so warm as to create discomfort for the person whose hair is being cut.

When there is an increase in the amount of friction that takes place between blades of electric shears, the amount of work which must be done by the motor which drives the shears also increases. The increased load places an extra burden upon the motor that reduces its efficiency and decreases its life.

Fouling of blades of hair shears causes another problem in that the fouling material, namely, oils, dirt, hair particles and the like, inhibit the free flow or air through the blades. The free flow of air is important because that is the primary manner in which heat is dissipated from moving blades. Thus, inhibited air flow increases the problems arising from an excessive increase in operating temperature.

It can be seen that it is important to keep the blades of shears clean. It can also be seen that it would be advantageous to lubricate the blades to decrease friction. Accordingly, it would be highly desirable to have a cleaning composition and method for cleaning and lubricating the blades of shears.

There are problems involved in cleaning shears. One problem is that body oils and oils from hair grooming aids are difficult to remove from the blades. In addition, these oils mix with dirt and other undesirable particles and make the mixture extremely difficult to remove from the blades. In general, oily substances cling to the blades and are not easily removed by wiping or agitation.

Another problem in cleaning shears is that the cutting blades are very closely positioned with respect to one another. The close alignment of blades is essential for optimal cutting but hinders effective wiping or brushing of the spaces between the blades.

The two problems discussed immediately above may be solved by using a liquid to penetrate the hard-to-reach areas between the blades and dissolve and remove the oily fouling material. Accordingly, it would be highly desirable to have a cleaning composition and method that effectively removes oily substances from hard-to-reach areas of shears.

Water and aqueous solutions unsuitable for cleaning the blades of shears for several reasons. Water alone will have virtually no effect on oils or oily substances. The water in aqueous solutions causes oxidation or corrosion of metal blades. Oxidized or corroded blades will not perform desirably. Water or water-based solutions are particularly unsuitable for cleaning electric shears because the electricity-conductive properties of water may cause electrical shock or short circuiting of clipper components.

A solvent which is capable of dissolving oily substances and dirt which does not exhibit the harmful characteristics or water described above would be most appropriate for a cleaning solution. A petroleum based solvent would meet these requirements. Kerosene, in particular, has been used to clean shears. However, kerosene has a strong, unpleasant odor which makes it an undesirable cleaning product. Also, kerosene alone is ineffective as a lubricant. Accordingly, it would be highly desirable to have a cleaning composition that both cleans and lubricates and also has a pleasing aroma.

Human hair normally contains germs. It is undesirable to transmit these germs from one person to another. Thus, it is prudent to both clean hair shears and apply an antiseptic to the shears after each use to prevent the spread of germs. The use of an antiseptic also helps prevent the infection of any cut or abrasion that comes about when a person is having his or her hair groomed. Accordingly, it would be highly desirable to have an antiseptic cleaning composition that not only cleans and lubricates but also inhibits the spread of germs and infections caused by germs.

U.S. Pat. Nos. 4,759,867; 4,654,374; 4,632,72 and 3,882,038; and U.K. Patent Application GB 2 173 508A, disclose hard surface cleaners. While the metal surfaces of the blades of hair shears are hard surfaces, these hard surface cleaners are unsuitable for cleaning hair shears because these cleaners contain acid or water. The reasons why an aqueous solution is unsuitable as a cleaner have been enumerated above. An acid cleaner is unsuitable in and of itself because it would corrode the metal blades. Acid may also be harmful to the plastic casing which houses most shears' motors and mechanisms.

SUMMARY OF THE INVENTION

The present invention is directed to overcoming one or more of the problems set forth above. Briefly summarized, according to one aspect of the present invention, a cleaning solution contains an aliphatic hydrocarbon with a small amount of fragrance, and an antimicrobial agent. Shears are cleaned, in general, by immersing the blades of the shears in the cleaning compound, placing the blades in motion for five or six seconds while they are immersed in the compound and, finally, removing the shears and wiping off excess cleaner from the shear.

It is an object of the present invention to provide a cleaning composition that cleans and lubricates the blades of shears. This object is achieved by adding a silicone lubricant to a nonchlorinated aliphatic solvent.

It is also an object of the present invention to provide a cleaning composition that cleans blades and is a good lubricant at low and high temperatures. This object is achieved by adding a silicone lubricant and mineral oil to a nonchlorinated aliphatic solvent.

Another object of the present invention is to provide a cleaning composition that cleans and lubricates and has a pleasing aroma. A pleasant aroma is given to the compound by the addition of a small amount of fragrance to the nonchlorinated aliphatic solvent.

Still another object of the present invention is to provide a cleaning composition with antiseptic properties that inhibits the spread of germs. This object is achieved by the addition of a small amount of an antimicrobial agent.

A further object of the present invention is to provide a cleaning composition that does not rust or corrode the blades of shears which are cleaned. The solution of the present invention does not contain water and is non-acidic. The solution does not promote rust or corrosion on the metal blades of shears.

A still further object of the present invention is to provide a method for cleaning and lubricating hair shears. An additional object of the present invention is to provide a simple, easy method for cleaning and lubricating hair shears. The present invention provides a method of immersing shears in a cleaning, lubricating antimicrobial compound.

BRIEF DESCRIPTION OF THE DRAWING

The drawing illustrates a pair of electric clippers being immersed into a container filled with a cleaning solution in accordance with an embodiment of the invention.

DETAILED DESCRIPTION OF THE PREFERRED EMBODIMENT

Figure 1:
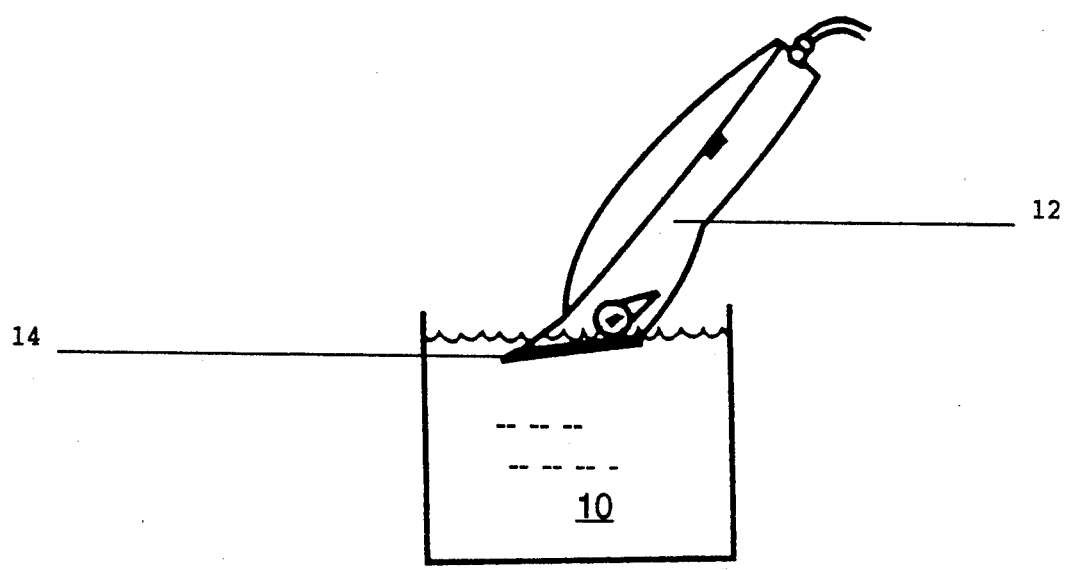

Referring to the drawing, the cleaning solution 10 of the present invention is a highly refined petroleum-based cleaner developed for everyday maintenance of hair shears, especially electric hair clippers 12. The cleaner 10 helps electric clippers 12 run cooler and more efficiently. The cleaning solution 10 will also prolong the life of electric shears and help keep the blades 14 sharp by removing dirt from the teeth of the blades 14. The cleaner 10 contains a petroleum-based solvent which easily dissolves the oil that causes hair and dirt to adhere to the teeth of the blades 14 of the clippers 12. The cleaner 10 is also suitable for manually-operated hair shears which are susceptible to the same dirt and debris as electric hair shears 12.

The cleaning solution 10 contains an aliphatic hydrocarbon as its base solvent. An aliphatic hydrocarbon is preferred over an aromatic, or cyclic, hydrocarbon as a base solvent for the cleaning solution because the latter type of hydrocarbon is likely to dissolve or distort the plastic casings of electric shears. A non-chlorinated solvent is used in the solution because chlorine is also likely to dissolve or distort the plastic casings of electric shears. The hydrocarbon can be further described as a petroleum distillate having a boiling range of from about 350 degrees to about 555 degrees F., a natural flash point greater than or equal to 140 degrees F., and a kauri butanol value of less than or equal to 30. An example of a suitable solvent is Low Odor Base Solvent manufactured by Ashland Chemical, Inc. By volume, the cleaning solution 10 contains about 85 to 95 percent aliphatic hydrocarbon. Using less than about 85 percent aliphatic hydrocarbon increases the cost of the solution because the costs of the other additives necessary to comprise the solution in sufficient total volume to be effective is comparatively greater.

The cleaning solution 10 also contains about 4 to 12 percent silicone. The silicone should have a viscosity in the range of 100–1,000 cs. measured at 77 degrees F. Preferably, the silicone is a 350 cs. viscosity dimethylpolysiloxane, such as DOW CORNING 200 fluid. When more than about 12 percent silicone is used the cost of the cleaning solution increases with no great increase in lubricity. When less than about 4 percent silicone is used a loss of lubricity is possible. The silicone is a good metal to nonmetal lubricant.

The cleaning solution also contains about 1 to 20 percent mineral oil. Mineral oil mixes well with the other ingredients in the compound and is a good metal to metal lubricant. When more than about 20 percent mineral oil is used, the solution becomes too oily. When less than about 1 percent is used, the mineral oil becomes ineffective. Preferably, the mineral oil is pharmaceutical grade. The combination of both lubricants provide lubrication over a wide range of temperatures.

A fragrance can be added to the cleaning solution to impart a very pleasing aroma. Suitable fragrances are H-8607 Unisex and H-8593 Baby Powder. These are common denotations in the chemical industry for artificial fragrances. Preferably, the fragrance comprises from about 0.05 to about 0.8 percent by volume of the cleaning solution. At volumes below about 0.05 percent, the fragrance is not very noticeable, and at volumes about 0.8 percent, the fragrance is very strong and unnecessarily increases the cost of the solution.

An antimicrobial agent can also be added to the cleaning solution to kill and inhibit the growth of microbes. Preferably, the antimicrobial agent comprises from about 0.1 about to 5.0 percent by volume of the cleaning solution. At volumes below about 0.1 percent, the antimicrobial agent is ineffective, and at volumes above about 5.0 percent no additional benefits are gained.

The cleaning solution cleans, conditions and lubricates shears. The cleaning solution does not contain hazardous chlorinated solvents and has a flash point greater than or equal to 140 degrees F., making it a safer cleaner that leaves the shears thoroughly cleansed and lubricated. A fragrance added to the cleaning solution give the cleaning solution a very pleasant aroma.

The cleaning solution also contains a very proficient antimicrobial agent. The cleaner is designed for cleaning at ambient temperatures for dip, brush, wipe or spray methods of cleaning. The solution of the invention is a cleaner with a very mild fragrance that helps the shears run cooler longer and cut better, and helps the blades stay sharp by removing hair, grease, oil and dirt from the teeth of the blades. The solution is substantially free of water because non of the ingredients contain more than about 500 parts per million of water. The solution has a non-acidic, neutral pH because of the ingredients used. Thus, the solution does not promote rusting or corrosion or short circuiting of electrical components when electric shears are cleaned.

The clipper cleaning solution can be made by mixing 55 gallons of aliphatic hydrocarbon (deodorized) with 1 gallon, 350 cs. viscosity dimethylpolysiloxane such as DOW CORNING 200 fluid and 5 gallons of NF grade light mineral oil.

The aroma can be improved by adding 0.25 gallons (or 32 ounces) of a fragrance such as H-8607 Unisex or H-8593 Baby Powder. The microbe-inhibiting properties of the cleaning solution may be improved by adding about 2 to 10 pounds of an antimicrobial agent, for example an O-phenylphenol, such as DOWICIDE 1.

The cleaning solution is used to clean electric shears 12 by submerging cool electric hair clipper blades 14 in the cleaner 10, turning the clippers 12 on and letting the clipper blades 14 stand in the cleaner 10 for five to six seconds. The clippers are then turned off, excess cleaning solution 10 is wiped, shaken or similarly removed from the blades, and the clippers are ready for use.

While the invention has been described with particular reference to a preferred embodiment, it will be understood by those skilled in the art that various changes may be made and equivalents may be substituted for elements of the preferred embodiment without departing from the letter and spirit of the invention. For example, while the invention has been described with particular emphasis on electric hair shears, the cleaning solution is equally effective for other tools, electrical motors, implements and devices. In addition, many modifications may be made to adapt a particular situation and material to a teaching of the invention without departing from the essential teachings of the present invention.

As is evident from the foregoing description, certain aspects of the invention are not limited to the particular details of the examples illustrated, and it is therefore contemplated that other modifications and applications will occur to those skilled in the art. It is accordingly intended that the claims shall cover all such modifications and applications as do not depart from the true spirit and scope of the invention.

What is claimed is:

1. A hard surface cleaning solution comprising by volume: about 85 to 95 percent of a nonchlorinated aliphatic hydrocarbon
   having a boiling range of from about 350 degrees to about 550 degrees F., a natural flash point greater than or equal to 140 degrees F., and a kauri butanol value of less than or equal to 30;
   about 4 to 12 percent of dimethylpolysiloxane having a viscosity in the range of about 100 cs. to 1,000 cs. measured at a temperature of 77 degrees F.;
   about 1 to 20 percent of mineral oil; and about 0.1 to 5.0 percent of an anti-microbial agent.

2. The invention of claim 1, wherein said viscosity of said dimethylpolysiloxane is about 350 cs.

3. The invention of claim 1, further comprising about 0.05 to 0.8 percent of a fragrance.

4. A method for cleaning, lubricating and disinfecting hair shears having cutting blades comprising:
   immersing the cutting blades of the shears in a solution comprising about 85 to 95 percent of a nonchlorinated aliphatic hydrocarbon having a boiling range of from about 350 degrees to about 550 degrees F., a natural flash point greater than or equal to 140 degrees F., and a kauri butanol value of less than or equal to 30, about 4 to 12 percent of dimethylpolysiloxane having a viscosity in the range of about 100 cs. to 1,000 cs. measured at a temperature of 77 degrees F. about 1 to 20 percent of mineral oil, and about 0.1 to 5.0 percent of an anti-microbial agent;
   oscillating the cutting blades through a cutting motion at least once;
   allowing the cutting blades to remain immersed in said solution while fouling particles fall from said cutting blades;
   removing the shears from said solution; and
   removing excess said solution from the shears.

5. The invention of claim 4, wherein said viscosity of said dimethylpolysiloxane is about 350 cs.

6. The invention of claim 4, wherein said solution further comprises about 0.05 to 0.8 percent of a fragrance.

* * * * *